United States Patent
Cash

(10) Patent No.: US 7,445,604 B2
(45) Date of Patent: Nov. 4, 2008

(54) BLOOD SAMPLING KIT AND METHOD OF USING SAME

(75) Inventor: William Phillip Cash, Marietta, GA (US)

(73) Assignee: Biosensors International USA, Newport Beach, CA (US)

( * ) Notice: Subject to any disclaimer, the term of this patent is extended or adjusted under 35 U.S.C. 154(b) by 0 days.

(21) Appl. No.: 10/958,177

(22) Filed: Oct. 4, 2004

(65) Prior Publication Data
US 2006/0074350 A1   Apr. 6, 2006

(51) Int. Cl.
A61B 5/00 (2006.01)
B65D 81/00 (2006.01)
A61M 5/28 (2006.01)

(52) U.S. Cl. ............................ 600/575; 604/201
(58) Field of Classification Search ........... 600/573, 600/486, 575; 137/625.47; 222/387; 604/102, 604/131, 201, 248, 102.03, 110, 198, 246, 604/33, 30; 433/80, 116
See application file for complete search history.

(56) References Cited
U.S. PATENT DOCUMENTS

| | | | |
|---|---|---|---|
| 4,673,386 A | 6/1987 | Gordon | |
| 4,763,648 A | 8/1988 | Wyatt | |
| 5,086,783 A | 2/1992 | Macors et al. | |
| 5,197,875 A * | 3/1993 | Nerli | 433/80 |
| 5,374,401 A | 12/1994 | Von Berg | |
| 5,746,717 A * | 5/1998 | Aigner | 604/102.03 |
| 5,759,160 A | 6/1998 | Neese et al. | |
| 5,848,994 A * | 12/1998 | Richmond | 604/248 |
| 5,947,932 A | 9/1999 | Desecki et al. | |
| 5,961,472 A | 10/1999 | Swendson et al. | |
| 6,158,467 A | 12/2000 | Loo | |
| 6,364,847 B1 | 4/2002 | Shulze et al. | |
| 6,418,966 B2 | 7/2002 | Loo | |
| 6,457,488 B2 | 10/2002 | Loo | |
| 6,918,889 B1 * | 7/2005 | Brunel | 604/110 |
| 2001/0013370 A1 | 8/2001 | Loo | |
| 2002/0017328 A1 | 2/2002 | Loo | |

* cited by examiner

Primary Examiner—Max Hindenburg
Assistant Examiner—Brian Szmal
(74) Attorney, Agent, or Firm—Foley & Lardner LLP

(57) ABSTRACT

Kits and methods for closed-system sampling blood in patients are disclosed. The kit includes a four-port stopcock adapted to allow communication at least between two ports. The stopcock has a first port adapted to receive a syringe, a second port for communicating with an infusion solution reservoir, a third port for receiving a flush solution, and a fourth port for communication with a patient. The kit also includes at least one sampling site adapted to fluidically communicate with the fourth port and to be positioned between the four-port stopcock and the patient. At least one of the sampling sites is adapted to allow extraction of a fluid being communicated between the stopcock and the patient.

9 Claims, 5 Drawing Sheets

BLOOD SAMPLING KIT AND METHOD OF USING SAME

BACKGROUND OF THE INVENTION

The present invention relates generally to the field of medical devices. In particular, the present invention relates to kits for blood sampling and methods for using the kits.

Frequent blood sampling is often a required procedure for patients receiving fluids or medication through, for example, an IV and a catheter on the patient. Typical blood sampling requires tapping an IV line, an arterial line or a catheter and drawing fluid from the patient. In drawing the fluid, sufficient fluid in the IV line must first be drawn before a sample of blood can be extracted. In some patients, particularly neonates, such drawing of the blood and fluid can result in an unacceptable level of blood waste. Further, the risk of infecting the patient and/or the medical technician can exist.

To prevent these problems, closed-system blood sampling is desirable. Existing closed-system blood sampling systems, however, tend to be complex, requiring operation of multiple stopcocks, valves, and sampling sites. This complexity increases the risk of human error, leading to further medical complications.

Further, in pump-controlled systems, blood sampling typically requires supplementing of the system through an external flush after the blood has been drawn. A pump precludes the use of a built-in flush device, for example, on an arterial pressure transducer arrangement. Thus, external flushing requires that the system be opened to flush the line after blood sampling. Thus, the system may be susceptible to an increased risk of infection.

SUMMARY OF THE INVENTION

The disclosed embodiments provide kits and methods for closed-system sampling blood in patients. The kit allows for closed-system blood sampling and for closed-system flushing of the line after blood sampling for a patient on a pump, for example. The kit may be particularly beneficial for use in pump-based infusion systems and small patients, such as neonates. The kit allows blood sampling without interruption of the pump and minimizes blood waste during arterial sampling or venous sampling. One embodiment of the kit includes a four-port stop cock adapted to receive an infusion solution through one of the four ports to be delivered to a patient through a catheter, for example. A sampling site is positioned between a second port of the four-port stop cock and the catheter. A third port of the four-port stop cock is adapted to receive a syringe that may be sheathed to prevent undesired contact between the external environment and the closed system. The fourth port of the stop cock may be in communication with a closed saline solution for use in flushing the closed system.

One aspect of the invention relates to a blood sampling kit. The kit includes a four-port stopcock adapted to allow communication at least between two ports. The stopcock has a first port adapted to receive a syringe, a second port for communicating with a solution reservoir, a third port for receiving a flush solution, and a fourth port for communication with a patient. The kit also includes at least one sampling site adapted to fluidically communicate with the fourth port and to be positioned between the four-port stopcock and the patient. At least one of the sampling sites is adapted to allow extraction of a fluid being communicated between the stopcock and the patient.

As used herein, "sampling" includes removing a small amount of fluid for the purposes of testing, analyzing or storing.

A "kit" includes a set or subset of components adapted to function substantially together. A kit may be packaged as a set and may include a subset of a packaged set.

A "port", as used herein, is a connection for communication of fluid. A port may be an inlet or an outlet. Fluid may be communicated and guided between two components by entering one port and exiting through another port.

A "stopcock" is a device having multiple ports and selectively allows fluidic communication at least between two ports.

A "syringe" refers to a device adapted to draw in or eject out fluids.

A "solution" refers to a solution adapted to be supplied to a patient's blood stream. The solution may include infusion solutions including medication or fluids containing minerals to replenish a patient, for example. Solutions may also be adapted for flushing an arterial pressure monitoring line, for example.

A "reservoir" refers to a supply of fluid. The fluid may be stored for future use and may be accessible by another component.

As used herein, a "flush solution" is a fluidic solution adapted to flush, clean or sterilize certain components. The flush solution may include a saline solution, for example.

A "sampling site", as used herein, refers to a component which allows for the injection or withdrawal of a fluid from a line or tubing. A sampling site may be adapted to receive a blunt cannula or a needle to inject or withdraw fluid. As used herein, "sampling site" may also include a valve adapted to allow injection or withdrawal of fluids.

The stopcock may include a lever for selecting a desired communication at least between two ports. The kit may also include a tubing adapted to connect the four-port stopcock to the sampling site. The kit may further include a tubing adapted to connect the sampling site to a patient catheter.

In a particular embodiment, the kit also includes a sheathed syringe adapted to engage the first port. The sheathed syringe has a reservoir for holding a fluid. The sheathed syringe may include a silicone sheath.

As used herein, a "sheath" refers to a covering which substantially covers a component such as a syringe. The "sheath may be a flexible covering which conforms to the shape and size of the component being covered.

The kit may include two sampling sites, at least one of the two sampling sites being adapted to allow injection of a fluid for communication to the patient. At least one sampling site adapted to allow injection of a fluid may be positioned closer to the stopcock than at least one sampling site adapted to extract fluid.

In another aspect, a method of blood sampling includes drawing a fluid through a catheter port of a four-port stopcock into a syringe engaged to an axial port of the stopcock, the catheter port being in communication with a patient. A solution inlet port of the four-port stopcock is adapted to communicate with a reservoir of solution to be directed to the patient through the catheter port. The method also includes extracting a blood sample through a sampling site positioned between the catheter port and the patient, and returning the fluid from the syringe through the catheter port.

In a particular embodiment, the method also includes drawing a flush fluid through a saline port of the four-port stopcock into the syringe, the saline port being in communication with reservoir of flush fluid, directing the flush fluid from the syringe through the catheter port, and restoring communication between the solution inlet port and the catheter port.

In a particular embodiment, sufficient fluid is drawn to ensure availability of blood at the sampling site.

In another aspect, a method of flushing a line in a closed system includes drawing a flush fluid through a saline port of a four-port stopcock into a syringe engaged to an axial port of the four-port stopcock. The saline port is in communication with a reservoir of flush fluid, a catheter port of the four-port stopcock is in communication with a patient, and a solution inlet port of the four-port stopcock is adapted to communicate through a pump with a reservoir of infusion solution to be directed to the patient through the catheter port. The method also includes directing at least a portion of the flush fluid through the catheter port and restoring communication between the catheter port and the solution inlet port.

DETAILED DESCRIPTION OF THE PREFERRED EMBODIMENTS

Figure 1:
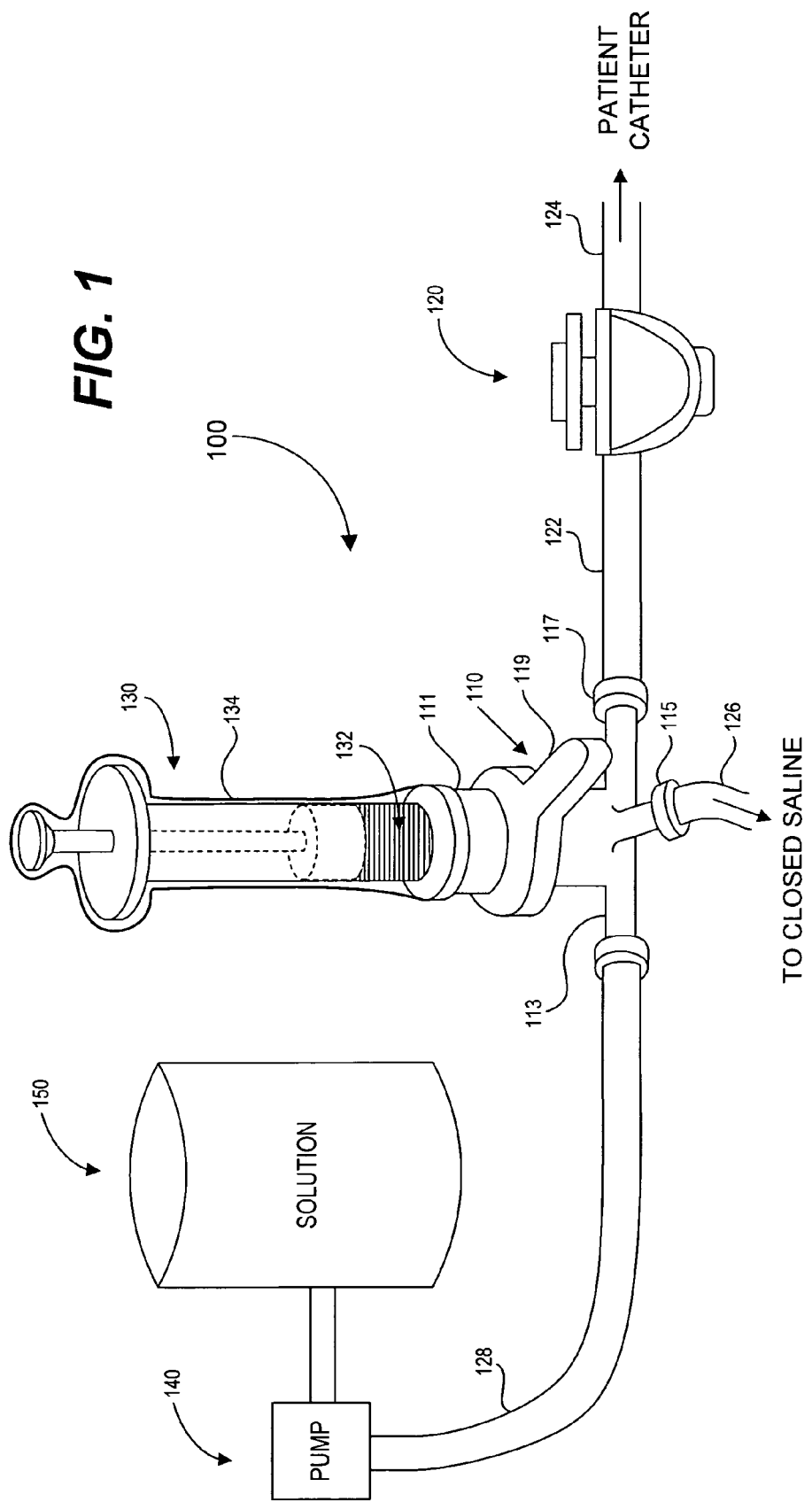
FIG. 1 is a diagrammatic illustration of an embodiment of a blood-sampling kit incorporated into a closed system.

Referring to FIG. 1, an embodiment of a blood-sampling kit is illustrated as incorporated into a closed system. The system 100 includes a four-port stopcock 110 and a sampling site 120 incorporated into a closed system for supplying a solution such as an infusion solution 150 to a patient (not shown). The infusion solution 150 may include any solution to be administered to a patient. Such solutions can include medication or mineral-enriched fluids required to re-hydrate a patient, for example. Such solutions may also include flush solutions for an arterial pressure monitoring line, for example. The infusion solution 150 may be supplied to the patient at a precisely controlled rate. To facilitate the control of the flow rate, a pump 140 is mounted between the reservoir of infusion solution 150 and the patient.

In a particular embodiment, the four-port stopcock is similar to that described in U.S. Pat. No. 6,418,966, which is hereby incorporated by reference in its entirety. One such stopcock is available through G L Medical in Beverly Hills, Calif., U.S.A. The stopcock 110 includes an axial port 111 which is adapted to receive a syringe 130 and is aligned with the axis of rotation of a lever 119. The axial port 111 may be provided with threading to securely engage the syringe 130, which may be provided with complementary threading.

The stopcock 110 is also provided with three non-axial ports, including a solution inlet port 113, a saline port 115 and a catheter port 117. Each port 113, 115, 117 is adapted to receive a tubing 128, 126, 122, respectively, to allow communication between the stopcock 110 and various components of the system 100. For example, in the illustrated embodiment, the solution inlet port 113 is in communication with a reservoir of infusion solution 150 to be supplied to the patient. Similarly, the saline port 115 is in communication with a reservoir of flush solution, such as saline, and the catheter port 117 is in communication with patient.

The stopcock 110 also includes a lever 119 to allow selection of communication paths among the four ports 111, 113, 115, 117. In a particular embodiment, the position of the lever 119 indicates which of the non-axial ports 113, 115, 117 is in communication with the axial port 111. Thus, in the configuration illustrated in FIG. 1, the axial port 111 is in communication with the saline port 115. In one embodiment of the four-port stopcock, communication between the two opposing non-axial ports, 113, 117 is maintained simultaneously with communication between the axial port and the saline port.

As noted above, the syringe 130 may be secured to the axial port 111 via complementary threadings provided on the syringe 130 and the axial port 111. The syringe 130 includes a cavity 132, the volume of which can be adjusted by, for example, pulling or pushing a piston within the cavity 132. In a particular embodiment, in order to maintain a closed system, the syringe may include a silicone sheath 134 surrounding substantially the entire syringe 130.

The sampling site 120 is positioned between the catheter port 117 of the stopcock 110 and the patient. Tubing 122 connects the catheter port 117 to the sampling site 120, and an additional tubing 124 is provided to complete the connection to the patient. The patient may have a catheter (not shown) to facilitate insertion and removal of the tube 124. In a particular embodiment, the sampling site 120 is a slitted, non-latex sampling site adapted to receive a blunt cannula. In this regard, the use of a sharp needle is avoided, thereby decreasing the risk of accidents involving either the patient or the medical technician. In other embodiments, the sampling site 120 includes a valve, thereby eliminating the need for a needle or a blunt cannula to inject or withdraw fluids.

Figure 2:
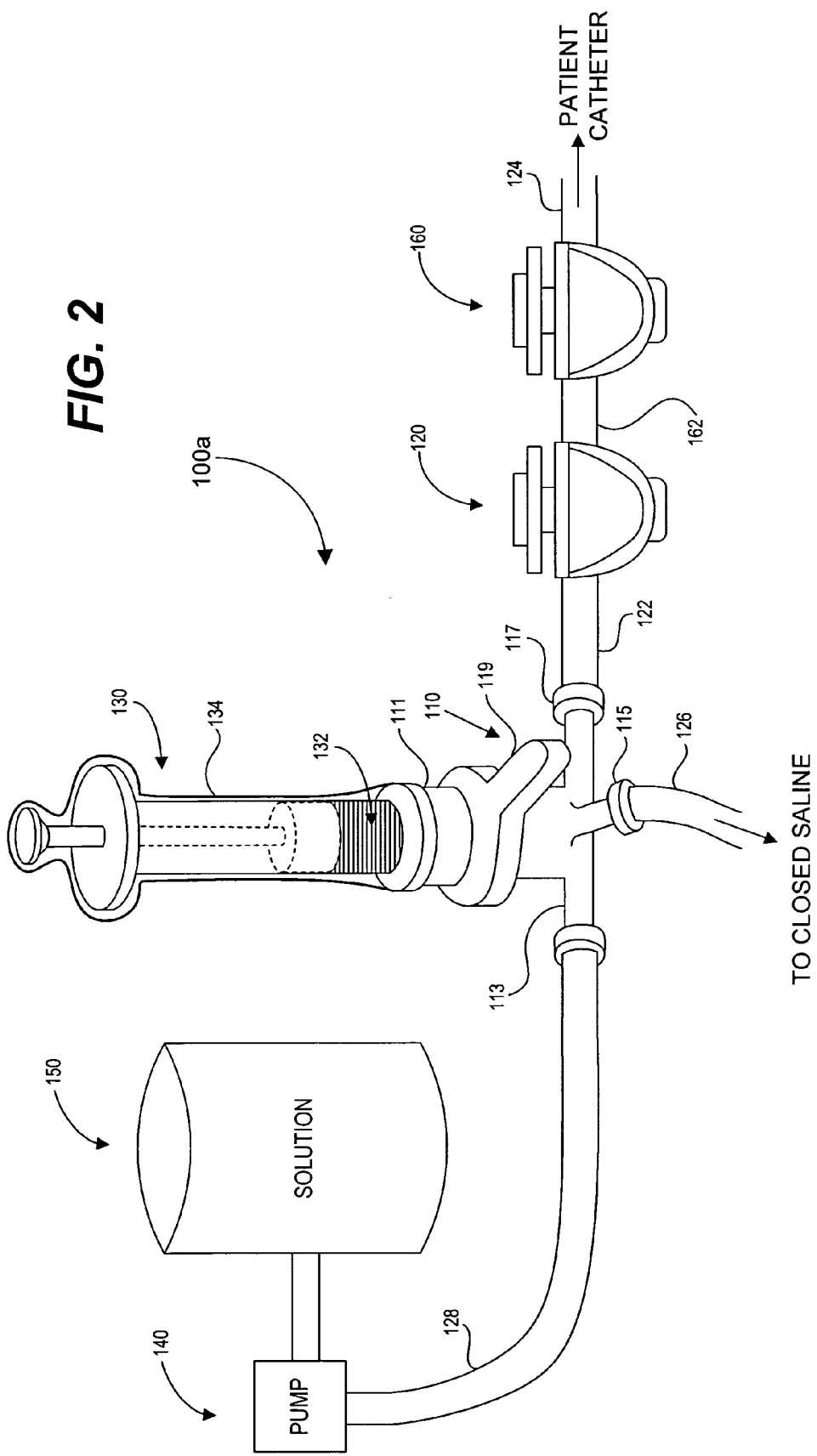
FIG. 2 is a diagrammatic illustration of another embodiment of a blood-sampling kit incorporated into a closed system.

In another embodiment, as illustrated in FIG. 2, a closed system 100a may include multiple sampling sites positioned between the stopcock 110 and the patient. In the embodiment illustrated in FIG. 2, a second sampling site 160 is positioned between the first sampling site 120 and the patient. An additional tubing 162 is provided to connect the two sampling sites 120, 160, and the tubing 124 now connects the second sampling site 160 to the patient.

Multiple sampling sites may be of particular importance for use in, for example, neonatal patients. Neonatal patients are typically on a pump. In this regard, using multiple sampling sites allows closed system flushing for such patients. Further, in a system with multiple sampling sites, the amount of blood drawn for clearance and the amount of flush fluid can be reduced. In this regard, the first sampling site 120 can be used to draw fluid into a syringe, such as a sheathed syringe. The amount of fluid drawn at the first sampling site 120 only needs to be sufficient to provide clearance at the second sampling site 160, which can be much closer to the catheter. Similarly, flush fluid is only required to be sufficient for flushing of the line between the second sampling site 160 and the catheter.

Figure 3:
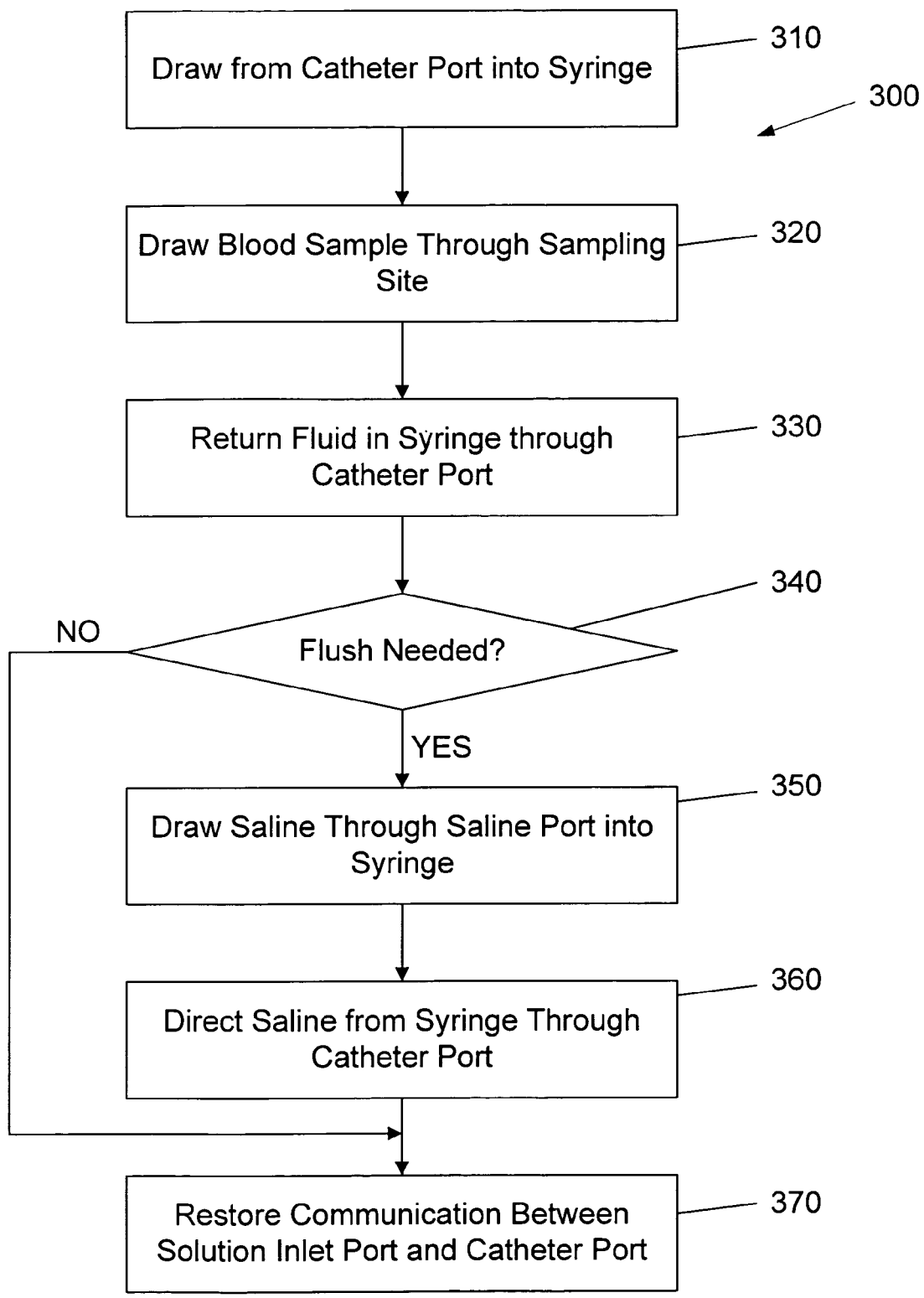
FIG. 3 is a flow chart illustrating an embodiment of a method of using the blood-sampling kit illustrated in FIG. 1.

Referring now to FIG. 3, a method of using the blood sampling kit incorporated into the embodiment illustrated in FIG. 1 will be described. The process 300 begins by drawing clearance fluid through the catheter port into the syringe mounted on the axial port (block 310). This can be achieved by positioning the lever 119 to be aligned with the catheter port 117 and expanding the volume of the cavity 132 of the syringe 130. Sufficient clearance fluid is drawn into the syringe to ensure that any infusion solution in the tubings between the sampling site 120 and the patient's blood stream is drawn past the sampling site 120.

Thus, a clean blood sample without any solution can be obtained from the sampling site 120, which is performed at block 320 using a blunt cannula, for example. In order to ensure no fluid is drawn into the blunt cannula from the syringe or the tubing between the stopcock 110 and the sampling site 120, the lever 119 may be turned to be aligned with the solution inlet port 113. Thus, the catheter port 117 is not in communication with any other port, and flow between the catheter port 117 and the sampling site 120 is restricted. In cases involving neonates, the amount of blood withdrawn can be limited by using the embodiment illustrated in FIG. 2, as described below.

Next, the lever 119 of the stopcock 110 is rotated to be again aligned with the catheter port 117, and the fluid in the syringe 130 can be returned to the patient through the catheter port (block 330). Thus, any blood mixed with the solution and included in the fluid drawn into the syringe is preserved and returned to the patient, thereby reducing blood waste.

A determination may be made as to whether the line between the stopcock 110 and the patient or the syringe 130 itself requires flushing (block 340). If the determination is made that no flushing is required, the process can proceed to block 370, and communication between the solution inlet port 113 and the catheter port 117 is restored. In this regard, the lever 119 of the stopcock 110 may be positioned to be aligned with the saline port 115. Alternatively, the lever 119 may not be aligned with any non-axial port 113, 115, 117 and may instead be positioned opposite the saline port 115.

If the determination is made at block 340 that a flush is required, as in most cases, a flush solution such as saline is drawn into the syringe 130 (block 350). This is achieved by positioning the lever 119 to be aligned with the saline port 115 and expanding the volume of the cavity 132 of the syringe 130. In this regard, the saline port 115 may be in communication with a reservoir of saline solution (not shown). In a particular embodiment, the reservoir of saline solution is a closed reservoir. The amount of saline drawn into the syringe should be sufficient to flush the tubing between the stopcock 110 and the patient.

The saline is then directed from the syringe 130 through the catheter port 117 (block 360). This is achieved by positioning the lever 119 to be aligned with the catheter port 117 and contracting the volume of the cavity 132 of the syringe 130. Thus, the components of the system 100 through which blood may have passed are flushed with the saline solution, and communication between the solution inlet port 113 and the catheter port 117 can be restored (block 370).

In certain cases, such as for neonatal patients or small infants, the amount of blood to be drawn is relatively small. For such cases, it may be desirable to draw as little clearance fluid as possible. In this regard, the embodiment illustrated in FIG. 2 may be used. The first sampling site 120 may be used to draw clearance fluid, and the second site 160 may be used to draw a clean blood sample. The clearance fluid may then be returned to the patient, and the syringe or cannula used for the clearance fluid can be disposed. The syringe 130 mounted on the axial port 111 of the stopcock 110 can be used to infuse a small volume of flush fluid into the tubing between the stopcock 110 and the patient. The saline port 115 may be used only occasionally to re-supply flush fluid to the syringe 130. An embodiment of such a method is illustrated in FIG. 4.

Figure 4:
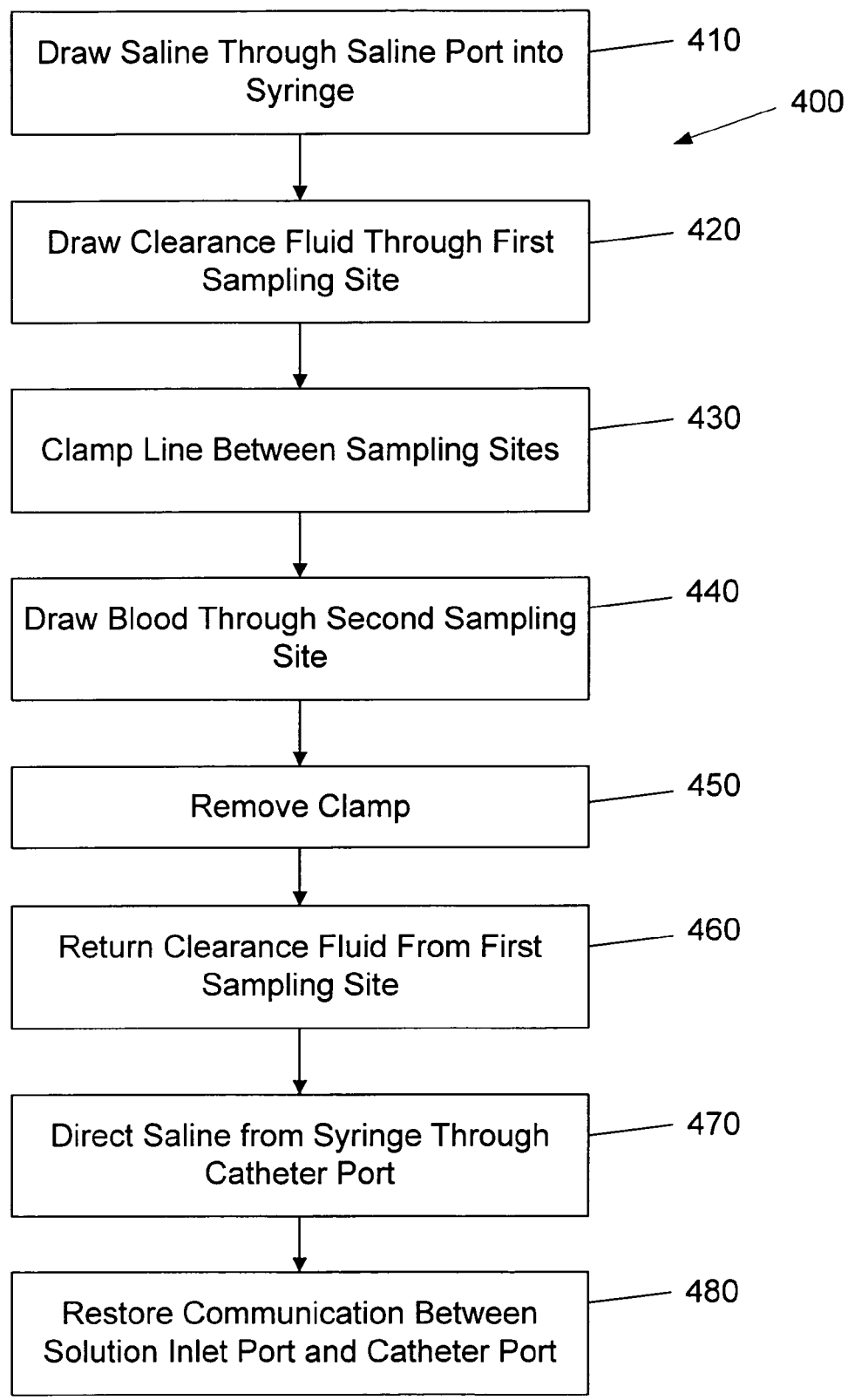
FIG. 4 is a flow chart illustrating an embodiment of a method of using the blood-sampling kit illustrated in FIG. 2.

Referring now to FIG. 4, a method of using the blood sampling kit incorporated into the embodiment illustrated in FIG. 2 will be described. The process 400 begins by drawing saline trough the saline port 115 into the syringe 130 (block 410). This is achieved by positioning the lever 119 to be aligned with the saline port 115 and expanding the volume of the cavity 132 of the syringe 130. Sufficient saline may be drawn into the syringe for multiple flushes. Accordingly, if sufficient saline exists in the syringe from a previous cycle, drawing of saline may not be required. Next, clearance fluid is drawn through the first sampling site 120 (block 420). This can be achieved by using a syringe and a blunt cannula (not shown). Sufficient clearance fluid is drawn into the syringe to ensure that any infusion solution in the tubing 124 between the second sampling site 160 and the patient's blood stream is drawn past the second sampling site 160.

Thus, a clean blood sample without any solution can be obtained from the second sampling site 160. This is accomplished by first blocking flow between the first sampling site 120 and the second sampling site 160 by, for example, clamping the tubing 162 between the two sampling sites 120, 160 (block 430). Now, at block 440, a blunt cannula, for example, can be used to draw blood through the second sampling site 160. After the blood has been drawn, the clamp can be removed (block 450). At block 460, the clearance fluid drawn at the first sampling site 120 at block 420 is returned to the patient. The syringe and the blunt cannula used at the first sampling site 120 can be discarded.

The saline is then directed from the syringe 130 through the catheter port 117 (block 470). This is achieved by positioning the lever 119 to be aligned with the catheter port 117 and contracting the volume of the cavity 132 of the syringe 130. Thus, the components of the system 100 through which blood may have passed are flushed with the saline solution, and communication between the solution inlet port 113 and the catheter port 117 can be restored (block 480).

Figure 5:
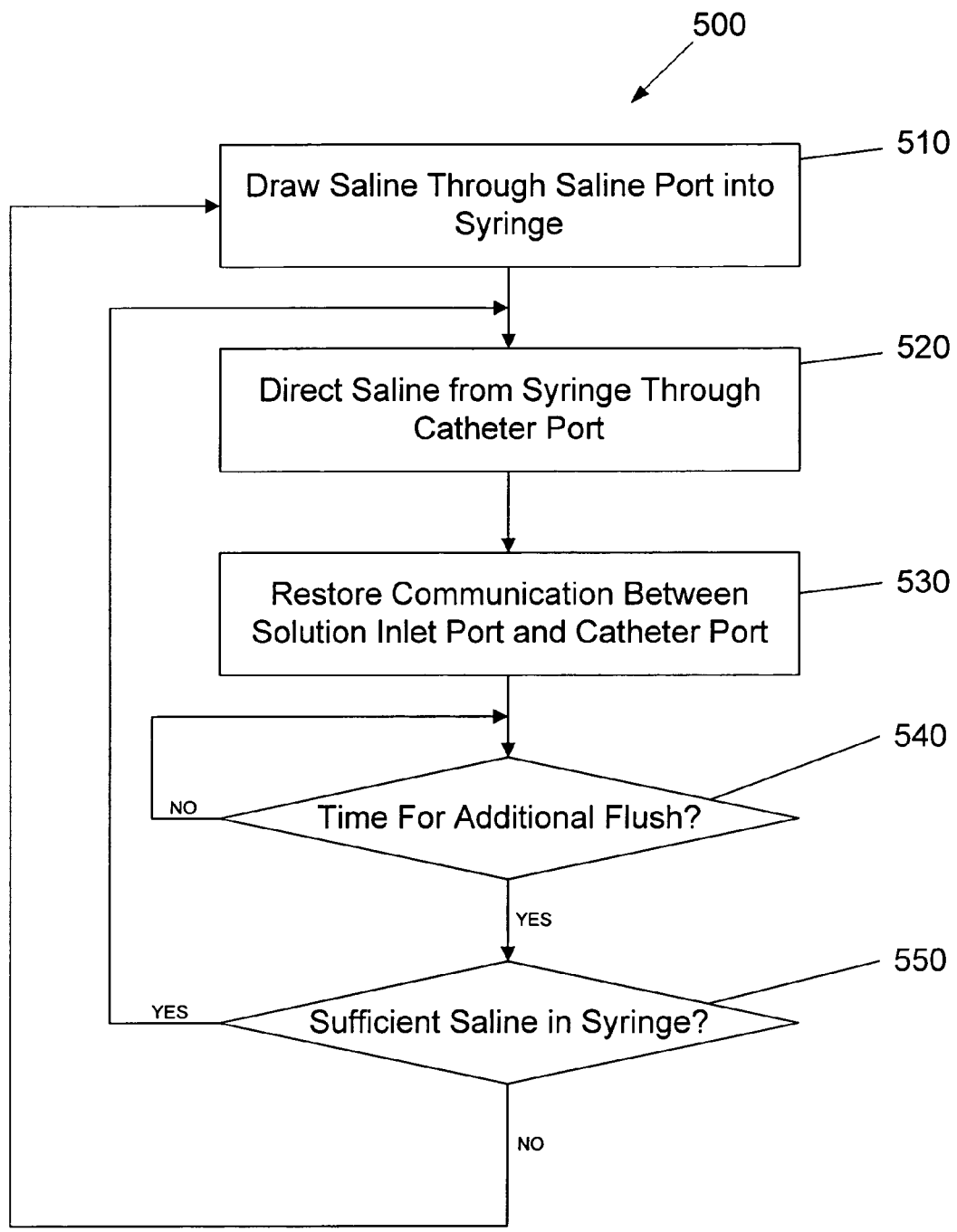
FIG. 5 is a flow chart illustrating an embodiment of a flushing method.

The kits and system described above also simplify the flushing process while maintaining a closed system. FIG. 5 illustrates one embodiment of a flushing method. The method 500 includes drawing a flush solution such as saline into a syringe 130 (block 510). As noted above, this is achieved by positioning the lever 119 to be aligned with the saline port 115 and expanding the volume of the cavity 132 of the syringe 130. In this regard, the syringe may be completely filled to capacity with the flush solution. Further, the syringe is adapted for multiple uses. In this regard, the syringe may include a sheathing to reduce the risk of infection.

The flush solution is then directed from the syringe 130 through the catheter port 117 (block 520) by positioning the lever 119 to be aligned with the catheter port 117 and contracting the volume of the cavity 132 of the syringe 130. The contracting of the volume of the cavity, corresponding to the amount of flush fluid delivered, should be sufficient to flush the components of the system 100 through which blood may have passed. In the case of neonatal patients, a limited amount of flush fluid should be delivered. Thus, some flush fluid may remain in the syringe 130.

Communication between the solution inlet port 113 and the catheter port 117 can then be restored (block 530). At block 540, a determination is made as to whether an additional flush is required. Additional flushes may be required if additional blood sampling is conducted after the restoration of communication between the solution inlet port and the catheter port at block 530. If additional flush is not yet required, the process remains at block 540. It is noted, however, that along the "NO" line from block 540 of FIG. 5, additional processes involving the kit may be conducted, such as blood sampling.

When the time for additional flushing has arrived, the method 500 proceeds to block 550, where a determination is made as to whether sufficient flush solution remains in the syringe for the flush. If sufficient flush fluid remains, the method returns to block 520, and additional flush solution is directed from the syringe through the catheter port. If sufficient flush solution does not remain in the syringe, the method 500 returns to block 510, and additional flush solution is drawn into the syringe.

Thus, the disclosed embodiments provide kits and methods for closed-system sampling blood and closed-system flushing for patients, particularly for patients on pumps, for fluid volume control and which reduce the risks of infections or accidents and minimize the amount of blood waste.

The foregoing description of embodiments of the invention has been presented for purposes of illustration and description. It is not intended to be exhaustive or to limit the invention to the precise form disclosed, and modifications and variation are possible in light of the above teachings or may be acquired from practice of the invention. The embodiments were chosen and described in order to explain the principles of the invention and its practical application to enable one skilled in the art to utilize the invention in various embodiments and with various modification as are suited to the particular use contemplated. It is intended that the scope of the invention be defined by the claims appended hereto and their equivalents.

What is claimed is:

1. A method of blood sampling, comprising:
    a) drawing a fluid through a catheter port of a four-port stopcock into a syringe engaged to an axial port of the stopcock, the catheter port being in fluid communication with a patient, a solution inlet port of the four-port stopcock being adapted to communicate with a reservoir of infusion solution to be directed to the patient through the catheter port, said solution inlet port not in fluid communication with said patient while said fluid is drawn through said catheter port, said drawing thereby causing blood from said patient to flow into said catheter port via said fluid communication and to reach a sampling site positioned between said catheter port and said patient;
    b) extracting a blood sample through said sampling site; and
    c) returning fluid from said syringe through said catheter port to said patient.

2. The method according to claim 1, further comprising:
    d) manipulating said stopcock to thereby establish communication between a saline port of said four-port stopcock and said syringe;
    e) drawing a flush fluid through said saline port of the four-port stopcock into said syringe, said saline port being in communication with a reservoir of flush fluid;
    f) manipulating said stopcock to thereby establish communication between said syringe and said catheter port;
    g) directing said flush fluid from said syringe through said catheter port; and
    h) manipulating said stopcock to thereby establish communication between said solution inlet port and said catheter port.

3. The method according to claim 1, wherein the fluid drawn in step a) includes the infusion solution.

4. The method according to claim 1, wherein step a) includes drawing sufficient fluid to ensure availability of blood at the sampling site.

5. The method according to claim 1, wherein the syringe is a sheathed syringe having a reservoir for holding a fluid.

6. The method according to claim 5, wherein said syringe includes a silicone sheath.

7. The method according to claim 1, wherein the solution inlet port is adapted to communicate with the infusion solution reservoir through a pump.

8. A method of blood sampling in a system including a four-port stopcock and at least two sampling sites, the stopcock having an axial port adapted to receive a syringe, a solution inlet port for communicating with a reservoir of infusion solution, a saline port for receiving a flush solution, and a catheter port for communication with a patient, said sampling sites being positioned serially between said catheter port and a patient, said method comprising:
    a) drawing a clearance fluid through a first sampling site, thereby causing blood to flow from said patient to a second sampling site, said drawing sufficient to provide access to blood at a second sampling site said second sampling site being positioned closer to the patient than said first sampling site;
    b) blocking flow between said first sampling site and said second sampling site; and
    c) drawing blood through said second sampling site;
    d) restoring flow between said first sampling site and said second sampling site; and
    e) returning said clearance fluid to the patient.

9. The method according to claim 8, further comprising:
    f) directing a flush fluid from the syringe on the axial port through the catheter port; and
    g) restoring communication between the solution inlet port and the catheter port.

* * * * *